(12) United States Patent
Bhuyan et al.

(10) Patent No.: US 11,123,048 B2
(45) Date of Patent: *Sep. 21, 2021

(54) INTEGRATED SYSTEM FOR ULTRASOUND IMAGING AND THERAPY

(71) Applicant: The Board of Trustees of the Leland Stanford Junior University, Stanford, CA (US)

(72) Inventors: Anshuman Bhuyan, Milpitas, CA (US); Jung Woo Choe, Sunnyvale, CA (US); Amin Nikoozadeh, Palo Alto, CA (US); Butrus T. Khuri-Yakub, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 457 days.

This patent is subject to a terminal disclaimer.

(21) Appl. No.: 16/150,044

(22) Filed: Oct. 2, 2018

(65) Prior Publication Data

US 2019/0076130 A1 Mar. 14, 2019

Related U.S. Application Data

(63) Continuation of application No. 14/793,280, filed on Jul. 7, 2015, now Pat. No. 10,123,782.
(Continued)

(51) Int. Cl.
*A61B 8/00* (2006.01)
*A61N 7/00* (2006.01)
(Continued)

(52) U.S. Cl.
CPC .............. *A61B 8/54* (2013.01); *A61B 8/4483* (2013.01); *A61N 7/00* (2013.01); *A61N 7/02* (2013.01);
(Continued)

(58) Field of Classification Search
CPC .......... A61B 8/54; A61B 8/4483; A61N 7/02; A61N 7/00; A61N 2007/0052;
(Continued)

(56) References Cited

U.S. PATENT DOCUMENTS 3,636,372 A    1/1972  Hujita et al.
5,984,881 A   11/1999  Ishibashi et al.
(Continued)

OTHER PUBLICATIONS

Francis J. Fry, Narendra T. Sanghvi, Richard S. Foster, Richard Bihrle, and Carl Hennige. "Ultrasound and microbubbles: their generation, detection and potential utilization in tissue and organ therapy experimental", Ultrasound in medicine & biology, 21(9): pp. 1227-1237, 1995.

(Continued)

*Primary Examiner* — Peter Luong
(74) *Attorney, Agent, or Firm* — Knobbe, Martens, Olson & Bear, LLP

(57) ABSTRACT

Ultrasound imaging and therapy with the same array of capacitive micromachined ultrasonic transducers is provided. The electronics includes a per-pixel switch for each transducer element. The switches provide an imaging mode driven completely by on-chip electronics and a therapy mode where off-chip pulsers provide relatively high voltages to the transducer elements.

22 Claims, 9 Drawing Sheets

Related U.S. Application Data

(60) Provisional application No. 62/021,341, filed on Jul. 7, 2014.

(51) Int. Cl.
 *B06B 1/02* (2006.01)
 *A61N 7/02* (2006.01)

(52) U.S. Cl.
 CPC .......... *B06B 1/0215* (2013.01); *B06B 1/0292* (2013.01); *A61N 2007/0021* (2013.01); *A61N 2007/0052* (2013.01); *B06B 2201/76* (2013.01)

(58) Field of Classification Search
 CPC .......... A61N 2007/0021; B06B 1/0215; B06B 1/0292; B06B 2201/76
 See application file for complete search history.

(56) References Cited

U.S. PATENT DOCUMENTS

| | | | |
|---|---|---|---|
| 6,488,630 B1* | 12/2002 | Hand | A61N 7/02 600/459 |
| 6,508,774 B1 | 1/2003 | Acker et al. | |
| 7,063,666 B2 | 6/2006 | Weng et al. | |
| 8,715,186 B2 | 5/2014 | Slayton et al. | |
| 10,123,782 B2 | 11/2018 | Bhuyan et al. | |
| 2001/0044278 A1 | 11/2001 | Chiao et al. | |
| 2003/0233044 A1 | 12/2003 | Brock-Fisher | |
| 2005/0113694 A1 | 5/2005 | Haugen et al. | |
| 2008/0228075 A1 | 9/2008 | Fraser et al. | |
| 2009/0182233 A1 | 7/2009 | Wodnicki | |
| 2009/0240148 A1 | 9/2009 | Jeong et al. | |
| 2011/0054315 A1 | 3/2011 | Roberts et al. | |
| 2011/0088475 A1 | 4/2011 | Oguzman et al. | |
| 2012/0041309 A1 | 2/2012 | Coussios et al. | |
| 2013/0144165 A1 | 6/2013 | Ebbini et al. | |
| 2014/0058294 A1 | 2/2014 | Gross et al. | |
| 2014/0114190 A1 | 4/2014 | Chiang et al. | |
| 2014/0288428 A1 | 9/2014 | Rothberg et al. | |
| 2014/0316269 A1 | 10/2014 | Zhang et al. | |
| 2015/0011880 A1 | 1/2015 | Kim et al. | |
| 2015/0305821 A1 | 10/2015 | Lacoste et al. | |
| 2016/0000412 A1 | 1/2016 | Bhuyan et al. | |

OTHER PUBLICATIONS

Grondin et al. "Real-time Monitoring of High Intensity Focused Ultrasound (HIFU) Ablation of In Vitro Canine Livers Using Harmonic Motion Imaging for Focused Ultrasound (HMIFU)." Journal of Visualized Experiments. Nov. 2015, pp. 1-7.

Miklós Gyöngy and Constantin-C. Coussios, "Passive cavitation mapping for localization and tracking of bubble dynamics", J. Acoust. Soc. Am. 128 (4), Oct. 2010.

Kennedy et al. "Localization and Interpretation of Bubble Activity during HIFU Exposure." AIP Conference Proceedings 1113, 68 (2009); https://doi.org/10.1063/1.3131473.

Li et al. "A New Active Cavitation Mapping Technique for Pulsed HIFU Applications—Bubble Doppler." *IEEE Trans Ultrason Ferroelectr Freq Control*. Oct. 2014; 61(10): pp. 1698-1708.

J.J. Macoskey, S.W. Choi, T.L. Hall, E. Vlaisavljevich, J.E. Lundt, F.T. Lee Jr, E. Johnsen, C.A. Cain, and Z. Xu, "Using the cavitation collapse time to indicate the extent of histotripsy-induced tissue fractionation", Physics in Medicine & Biology, 63(5):055013, 2018.

Adam D Maxwell, Tzu-Yin Wang, Charles A Cain, J Brian Fowlkes, Oleg A Sapozhnikov, Michael R Bailey, and Zhen Xu, "Cavitation clouds created by shock scattering from bubbles during histotripsy", The Journal of the Acoustical Society of America, 130(4):pp. 1888-1898, 2011.

Zhou, Yu-Feng. "High intensity focused ultrasound in clinical tumor ablation," *World J. Clin. Oncol*. Jan. 10, 2011; 2(1): pp. 8-27.

Jessica E. Parsons, Charles A. Cain, Gerald D. Abrams, and J. Brian Fowlkes, "Pulsed Cavitational Ultrasound Therapy for Controlled Tissue Homogenization", Ultrasound in Medicine & Biology, 32(1): pp. 115-129, 2006.

Vasant A. Salgaonkar, Saurabh Datta, Christy K. Holland, and T. Douglas Mast, "Passive cavitation imaging with ultrasound arrays", J. Acoust. Soc. Am. 126 (6), Dec. 2009.

Armen P. Sarvazyan, Oleg V. Rudenko, Scott D. Swanson, J. Brian Fowlkes, and Stanislav Y. Emelianov, "Shear Wave Elasticity Imaging: A New Ultrasonic Technology of Medical Diagnostics", Ultrasound in Medicine & Biology, 24(9): pp. 1419-1435, 1998.

* cited by examiner

INTEGRATED SYSTEM FOR ULTRASOUND IMAGING AND THERAPY

CROSS REFERENCE TO RELATED APPLICATIONS

This application is a continuation of U.S. patent application Ser. No. 14/793,280, filed on Jul. 7, 2015, which claims the benefit of U.S. provisional patent application 62/021,341, filed on Jul. 7, 2014, the disclosures of each of which are hereby incorporated by reference in their entireties herein.

GOVERNMENT SPONSORSHIP

This invention was made with Government support under contract number R01HL117740-01A1 awarded by the National Institutes of Health. The Government has certain rights in this invention.

FIELD OF THE INVENTION

This invention relates to combined ultrasound imaging and therapy.

BACKGROUND

Ultrasound is used in medicine for both imaging and therapy. However, conventional ultrasound imaging and therapy approaches tend to require different systems for imaging and therapy. This can undesirably lead to increased time in diagnosis and treatment of the patient. Also, a physician may need to use a "best guess" strategy for therapy/stimulation of a particular region because of lack of real-time spatial and anatomical information of the region of interest. Therefore, methods of providing both imaging and therapy with the same system have been considered.

One example is considered in US 2009/0240148. In this work, the system includes both an imaging array and a therapy array integrated to form a composite array. Thus some parts of the array are dedicated to imaging and other parts of the array are dedicated to therapy.

Another example is considered in US 2014/0288428. In this work, the system includes a single transducer array used for both imaging and therapy, and all corresponding electronics is monolithically integrated with the transducer array.

SUMMARY

We have found that known approaches for providing both imaging and therapy in a single ultrasound system have undesirable drawbacks. In cases where a composite imaging array is used, extra complexity may be incurred by having some parts of the array dedicated to imaging and other parts of the array dedicated to therapy. In cases where full monolithic integration is employed, the on-chip power dissipation caused by the relatively high-voltage pulsers used for ultrasound therapy can be excessive.

This work alleviates the above-described drawbacks by providing a transducer configuration where the electronics includes a per-pixel switch for each transducer element. The switches provide an imaging mode driven completely by on-chip electronics and a therapy mode where off-chip pulsers provide relatively high voltages to the transducer elements.

Furthermore, it is important that the transducer elements be capacitive micromachined ultrasonic transducer (CMUTs), as opposed to piezoelectric transducers. One reason for this is that CMUTs dissipate far less heat in the therapy mode than piezoelectric transducer do. Another important factor is the surprising ability of a single CMUT design to work well for both imaging and therapy.

Some design considerations relating to CMUT design for both imaging and therapy follow. Ultrasound imaging has typically used transducers that operate in frequency ranges from 5-15 MHz. Two-dimensional CMUT arrays operating at 5 MHz have been developed to achieve volumetric imaging. The wide bandwidth nature of the transducer (low Q) provides superior imaging qualities due to better image resolution, when compared to conventional piezoelectric transducers.

However, using the same transducer for therapy has its trade-off—one being inferior penetration performance (typical transducers used for therapeutic application operate at 1 MHz) and the other being the fact that these transducers have a low mechanical Q thigh Q devices are desirable for therapeutic application). One way to compensate for the low Q is to use series inductors and tune them to achieve as high a Q possible. The benefit of doing this is the reduced voltage drive requirements of the pulsers. The drive voltage seen by the transducer is Q times amplified allowing for reduced power dissipation by the driving circuit. Such a scheme can make dual-modality of the CMUT system more practical, where, in one mode, we use the wide bandwidth nature of CMUTs to achieve high resolution imaging, and in the other mode, we use the inductors to tune the front end transducers to achieve high Q, allowing for a better therapeutic system.

This approach has widespread applications. Any ultrasound application that requites Simultaneous imaging and HIFU (high intensity focused ultrasound)/therapy capabilities can benefit. For example, applications include ultrasound imaging and neural stimulation.

Significant advantages are provided. At present, ultrasound imaging and therapy/stimulation usually needs to be done using different devices leading to increased time in diagnosis and treatment of the patient. Also, physicians may need to use a "best guess" strategy to determine the treatment location since it does not have real-time spatial and anatomical information of the region of interest. Use of the present approach will allow one to remove such uncertainties in the actual region of interest and improve the speed of diagnosis/treatment.

DETAILED DESCRIPTION

This work provides a novel method for integrating ultrasound imaging and therapy (or ultrasound neuromodulation)

using the same ultrasound transducer array integrated with electronics. Having the same device for both purposes can be very beneficial. However, there are challenges in incorporating imaging and continuous-wave (CW) or quasi-CW ultrasound application capabilities in a single integrated chip (such as power dissipation, and area requirements). This work provides a solution to these challenges using switches in the integrated circuit that can switch between an imaging mode (Mode I) and a CW/quasi-CW CW mode (Mode II). The switches enable the use of external off-chip pulsers for Mode II allowing it to outsource the power dissipation to the back-end system.

A 2D CMUT array can be integrated with an IC (integrated circuit) that includes transceivers for using the integrated chip for imaging. The transceivers include transmit beam-formers that are capable of providing a high voltage (HV) pulse and receivers that signal condition the receive signals from the CMUT array. For Mode I, a single (or very short) HV pulse is used (duty cycle of the pulse is minuscule). However, for Mode II, multiple cycles of HV pulsing is desirable, to increase the time-averaged intensity of the focal spot. This leads to large power dissipation of the IC chip, if on-chip pulsers are used, since there are multiple elements pulsing. Therefore, using on-chip pulsers for Mode II applications is impractical.

This problem is alleviated by using HV switch(es) in each element, that can route the connection of the ultrasound transducer array element directly to an off-chip HV pulser. Though the overall power dissipation still remains high, the dissipation occurs at the back-end which is not near the patient. Utilizing these switches allow us to switch a single sensor array between Mode I and Mode II. Different elements can be pulsed at different phases to provide focusing in Mode II. In one implementation, we use 8 off-chip pulsers with equally spaced phases and distribute the elements amongst these 8 pulsers to enable focusing at a given Spot. With such a configuration, we can use the same integrated array for Mode I as well as for Mode II, as and when desired by the physician when performing a medical procedure.

Figure 1:
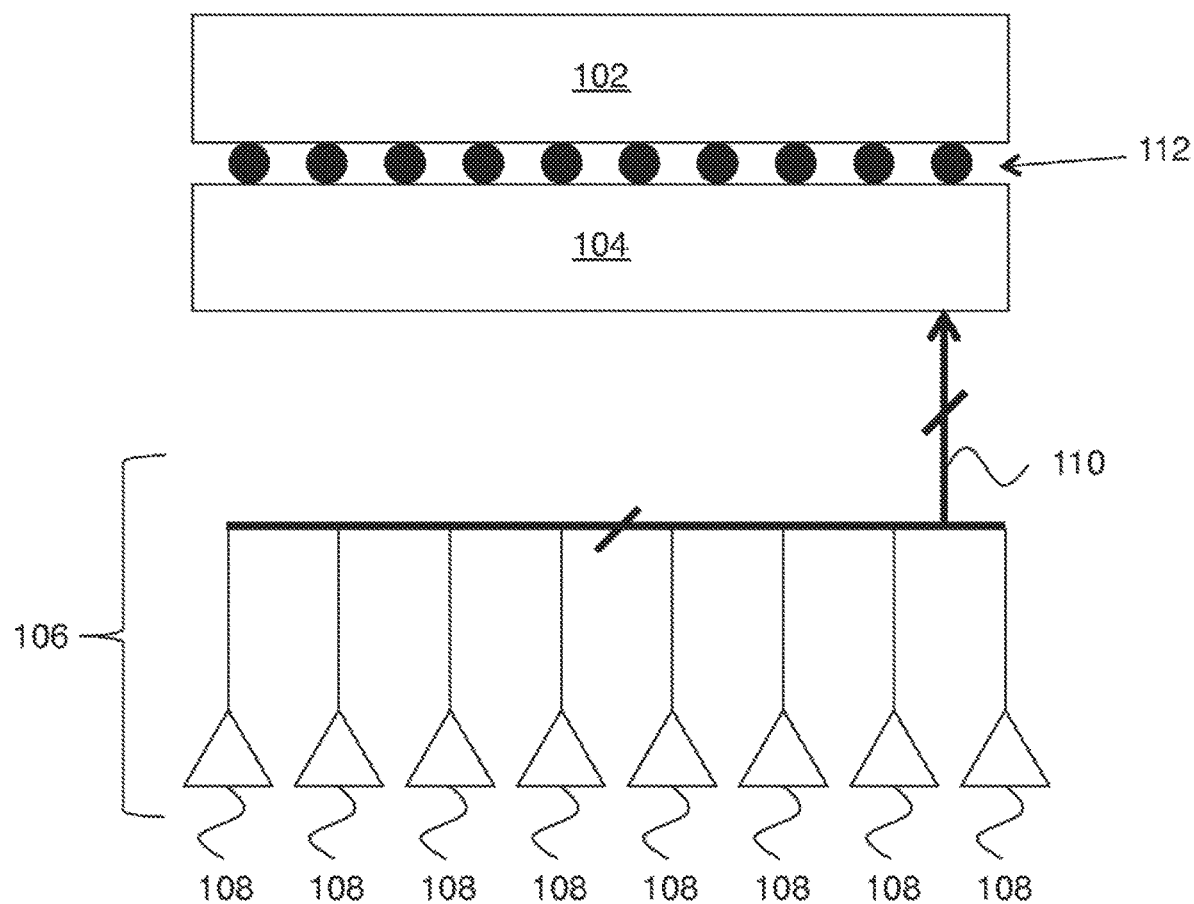
FIG. 1 shows an embodiment of the invention.

FIG. 1 shows an exemplary embodiment of the invention. In this example, a 2-D CMUT array 102 is flip chip bonded (112) to chip 104 that includes imaging electronics and the per-pixel switches. Off-chip pulsers 108 provide a high-voltage assembly 106 that is connected to chip 104 via bus 110. Bus 110 has one line for each pulser 108.

Figure 2:
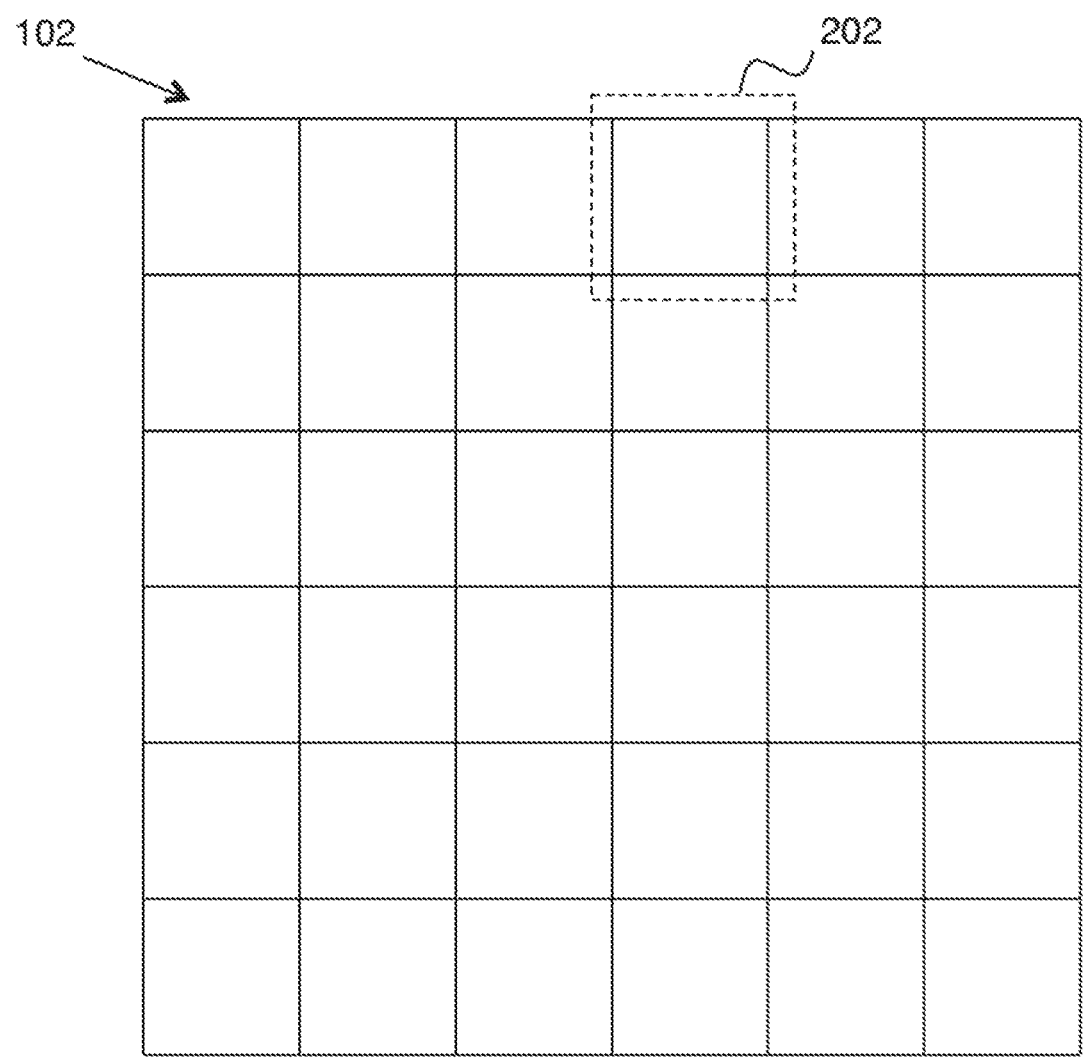
FIG. 2 shows a 2-D array of transducer elements.
Figure 3:
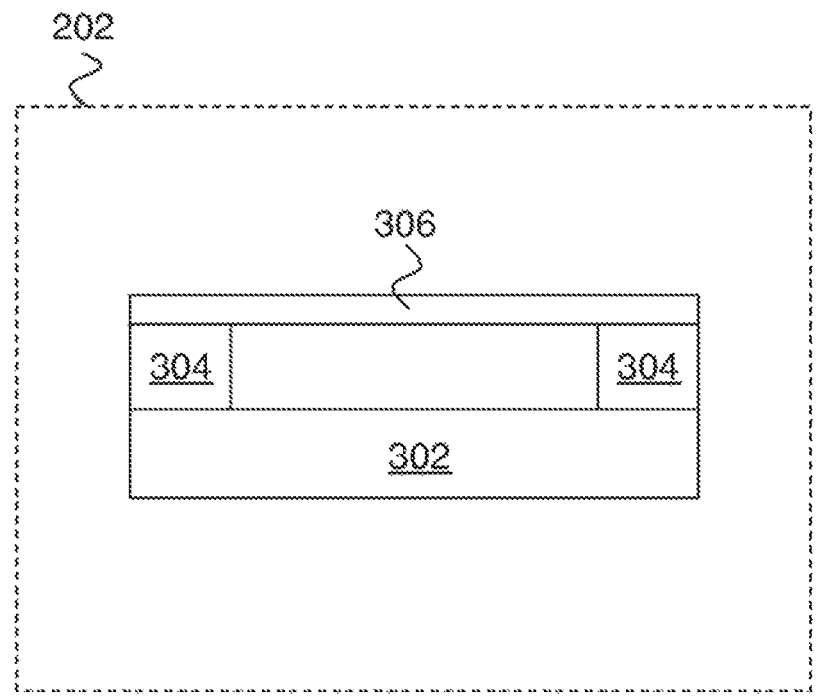
FIG. 3 shows one of the transducer elements of the array of FIG. 2.

FIG. 2 is a plan view of the 2-D array of transducer elements 102. One of the transducer elements is referenced as 202. FIG. 2 shows a 6×6 array of transducers, but any other 2D array dimensions can also be used. The low on-chip power dissipation of the present approach can enable large array sizes (e.g., 32×32 or larger). FIG. 3 shows transducer element 202 in more detail. As indicated above, the transducer elements are CMUTs. The general configuration for a CMUT is shown here, with 306 being an elastic membrane suspended above a substrate 302 by one or more support members 304.

Figure 4:
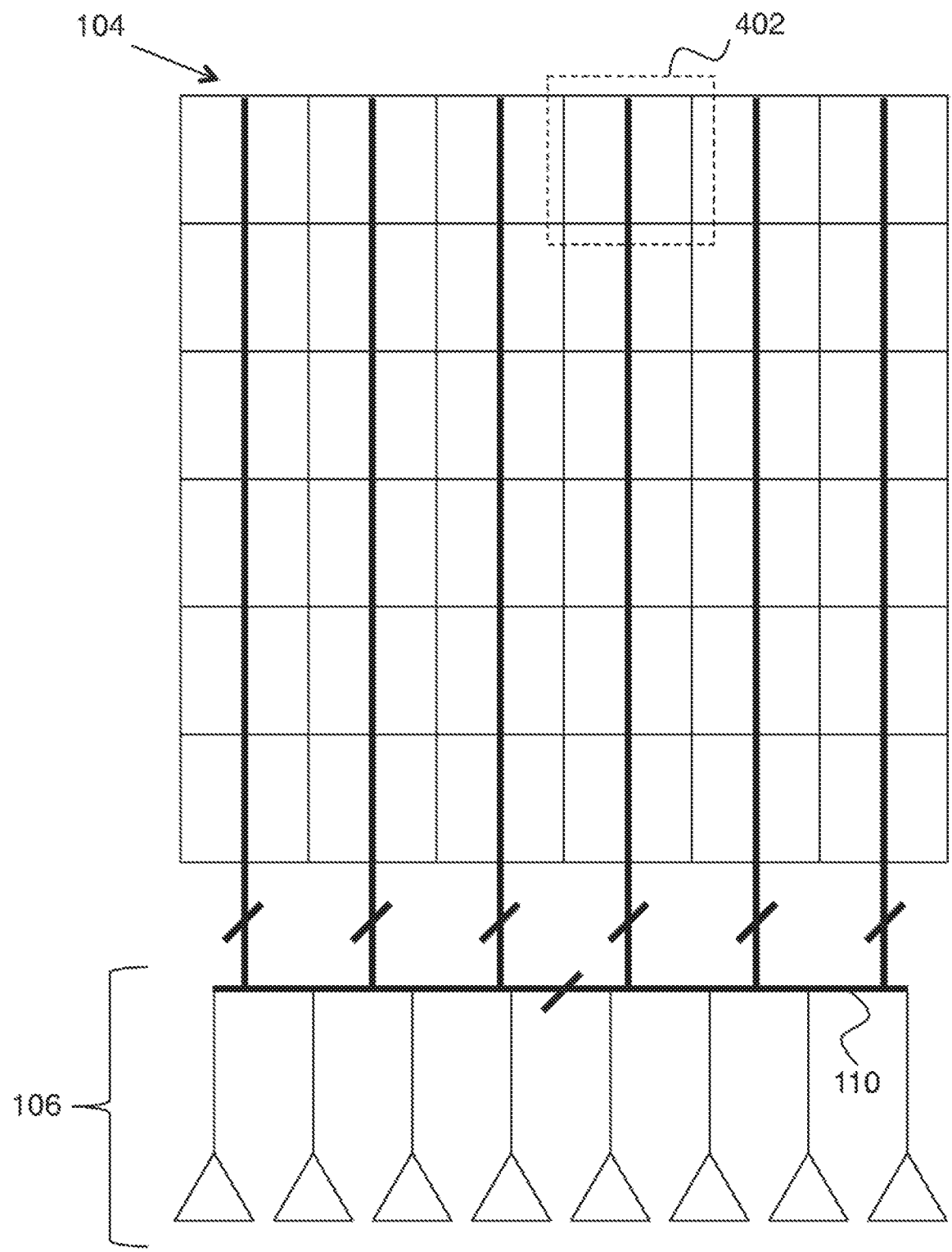
FIG. 4 shows circuitry to perform ultrasonic therapy with the 2-D array of transducer elements.
Figure 5:
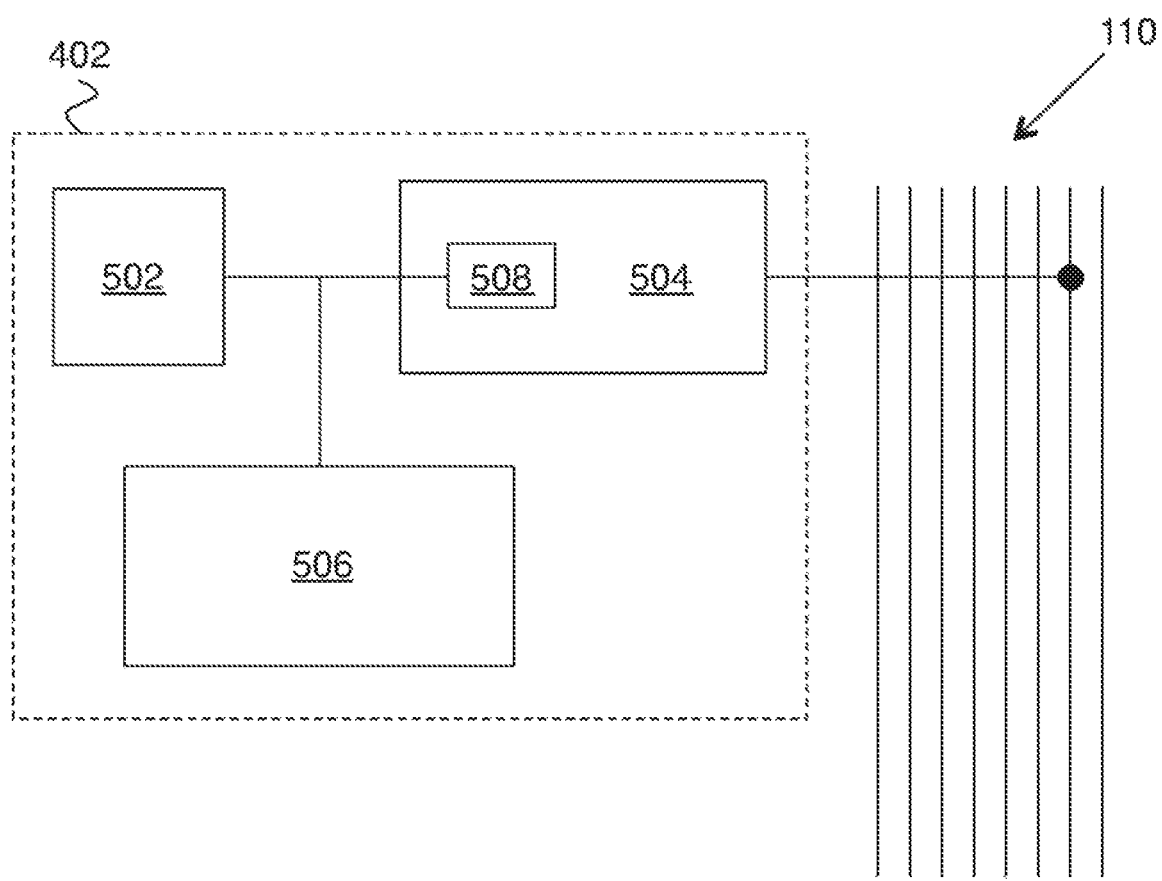
FIG. 5 is a more detailed view of per-pixel circuitry.

FIG. 4 shows circuitry to perform ultrasonic therapy with the 2-D array of transducer elements. Here chip 104 is regarded as having cells that correspond to the elements of transducer array 102. Bus 110 is shown being available at all cells, and one of these cells is referenced as 402. FIG. 5 is a more detailed view of cell 402. Here 502 is a flip chip pad that is connected to the corresponding transducer element of transducer array 102, 504 is the per-pixel switch, 506 is on-chip imaging circuitry, and 508 is an optional inductance in series with the CMUT capacitance that is present in preferred embodiments to provide electrical resonance in the therapy mode.

Figure 8:
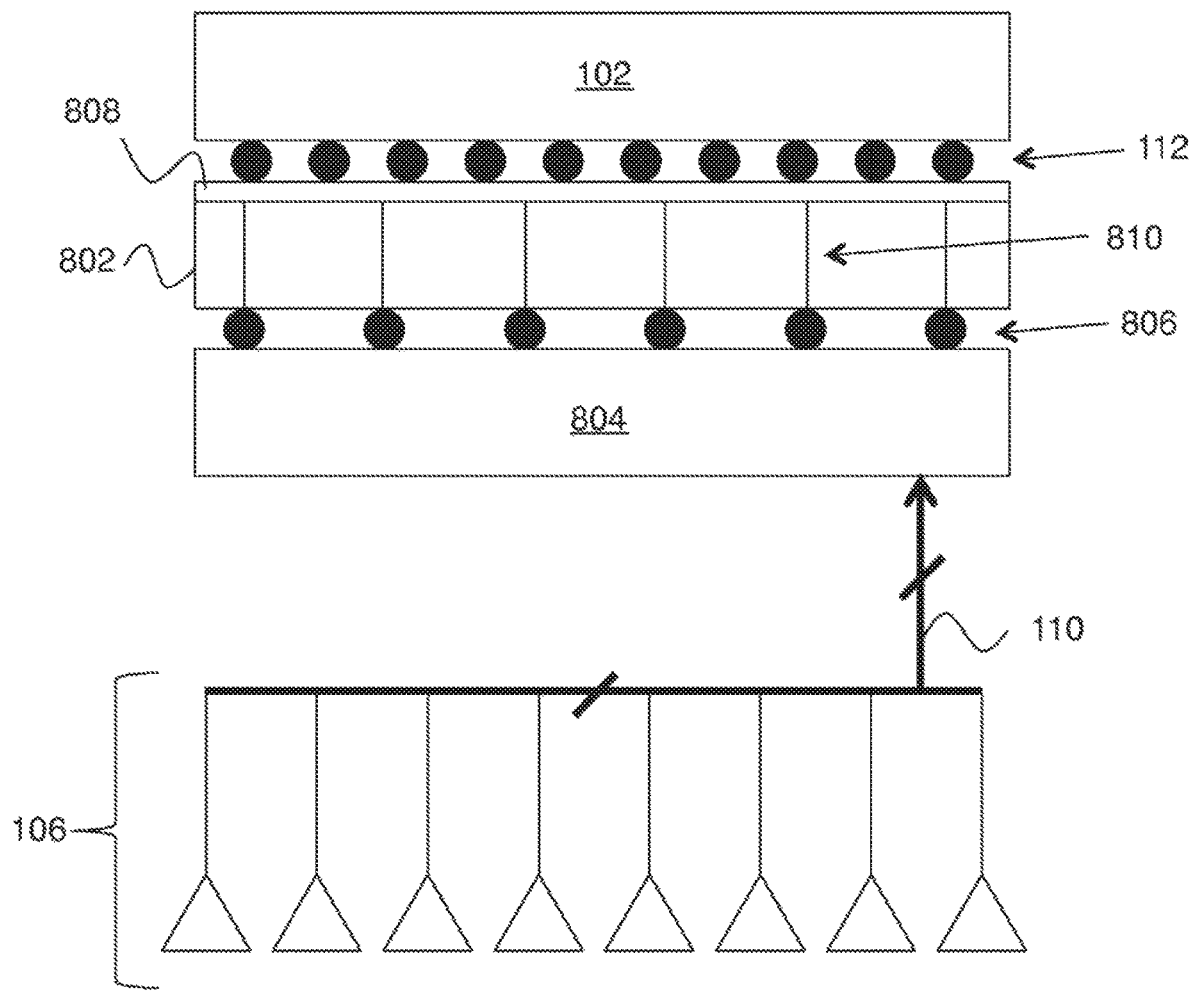
FIG. 8 shows another embodiment of the invention.
Figure 9:
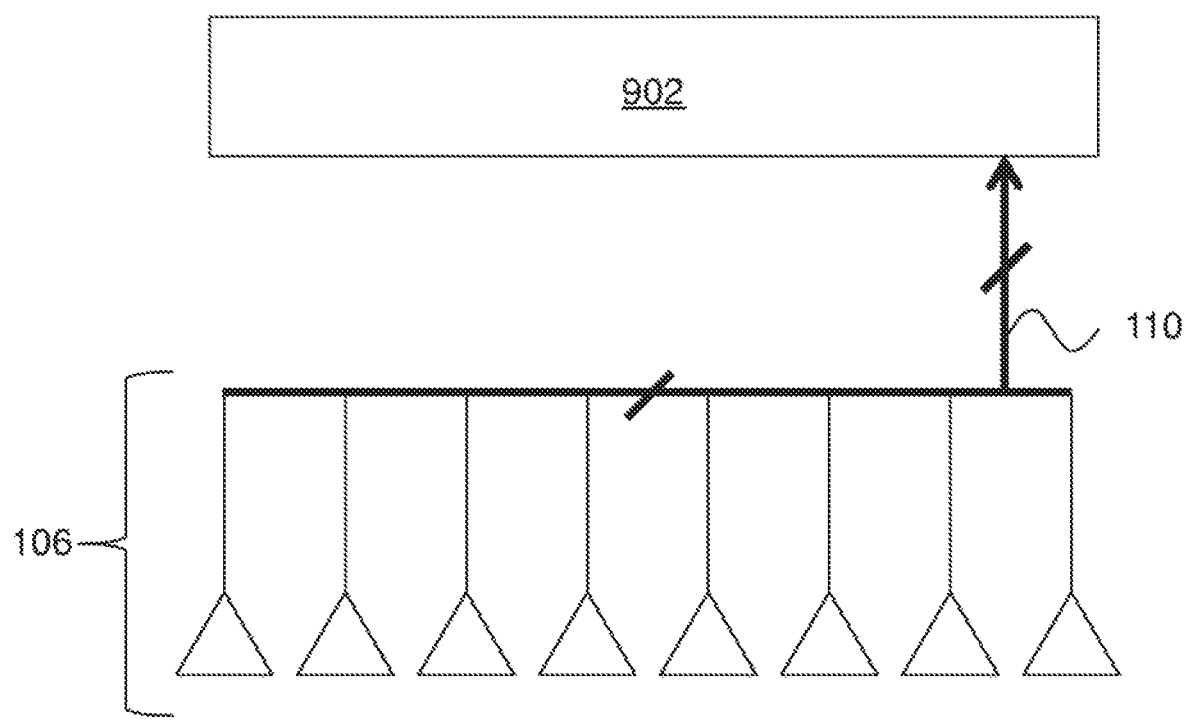
FIG. 9 shows a further embodiment of the invention.

Thus an exemplary embodiment of the invention is apparatus for ultrasonic imaging and therapy, where the apparatus includes:

1) a 2-D array of transducer elements monolithically integrated on a transducer chip (102), wherein each of the transducer elements is a capacitive micromachined ultrasonic transducer (FIG. 3);

2) first electronic circuitry (506) configured to perform ultrasonic imaging with the 2-D array of transducer elements, wherein the first electronic circuitry is integrated with the transducer chip (e.g., hybrid integration as on FIGS. 1 and 8, or monolithic integration as on FIG. 9);

3) second electronic circuitry (106) configured to perform ultrasonic therapy with the 2-D array of transducer elements, wherein the second electronic circuitry comprises one or more off-chip pulsers (108) disposed remotely from the transducer chip; and 4) mode switching circuitry (504) configured to switch operation of each of the transducer elements between an ultrasonic imaging mode and an ultrasonic therapy mode.

As indicated above, it is preferred that the second electronic circuitry include an inductor corresponding to each transducer element configured such that the combination of inductor and transducer element is electrically resonant at the ultrasound therapy frequency. This electrical resonance helps to compensate for the relatively low mechanical Q of the CMUT transducer elements. There are several options for the location of the series inductors. The inductors can be located inside block 504, e.g., 508 on FIG. 5. Another option is to have another die with just inductor arrays.

Figure 6:
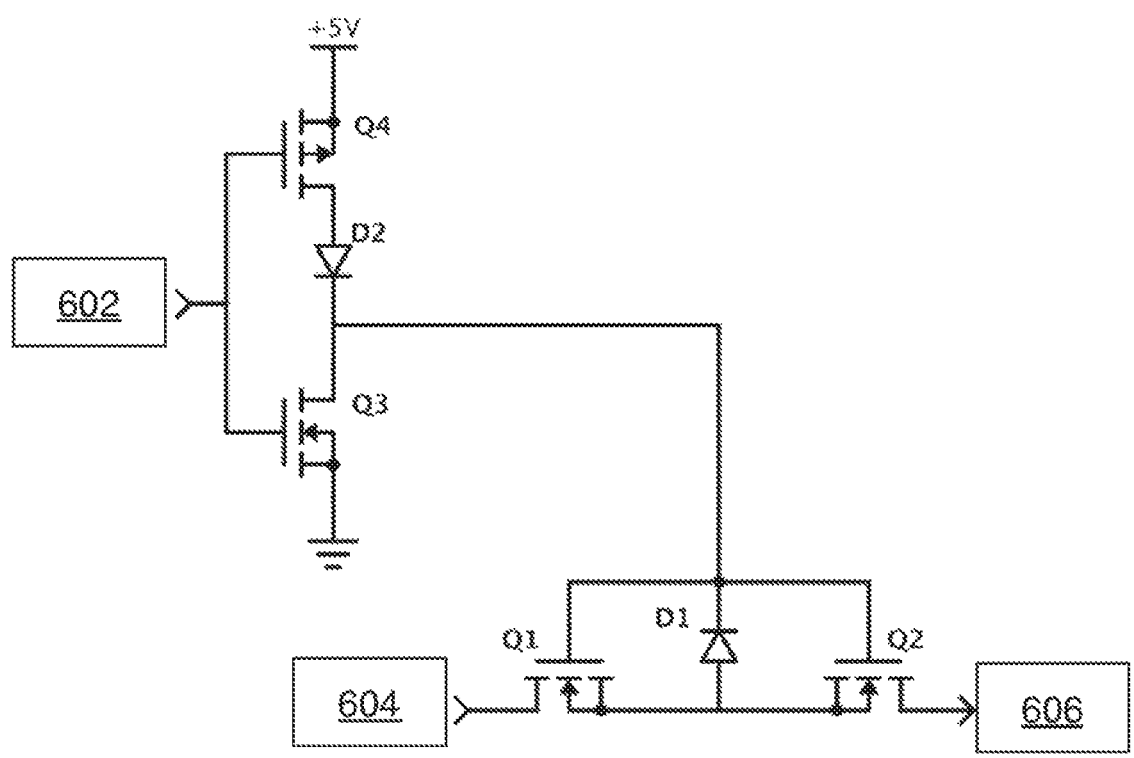
FIG. 6 shows a preferred circuit for mode switching.

FIG. 6 shows a preferred circuit 504 for mode switching, without the optional inductor 508. Here 602 is the control input to the switch, 604 is an input from the corresponding off-chip pulser, and 606 is a connection to the corresponding CMUT transducer element. In the circuit of FIG. 6, devices D2, Q3, Q1 and Q2 need to be high voltage devices (i.e., capable of handling the voltages provided at input 604 by the pulser), while devices D1 and Q4 can be low voltage devices. The net effect of this circuit configuration is to allow a drive voltage to be applied to transistors Q1 and Q2 that is greater than the gate-source voltage of any single transistor in the circuit. This configuration can be regarded as a first pair of series-connected transistors and a diode having an output that drives a second pair of series-connected transistors and a reverse-biased diode.

Figure 7:
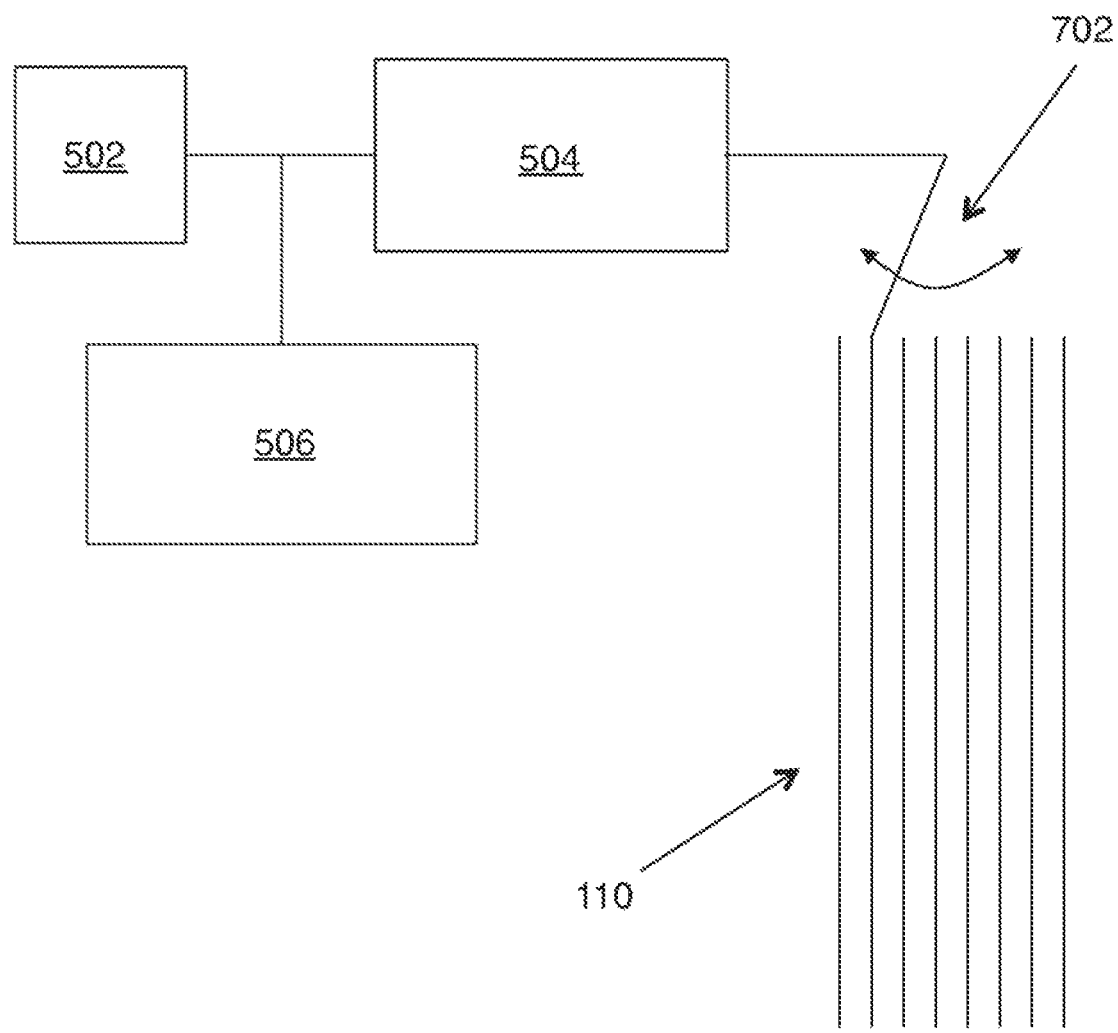
FIG. 7 shows a pixel switch configured to connect or disconnect its corresponding transducer element to a selectable one of the off-chip pulsers.

The off-chip pulsers 108 can be configured to provide inputs having distinct electrical phase. This can provide beam control for ultrasonic therapy. In some cases each pixel switch is configured to connect or disconnect its corresponding transducer element to a predetermined one of the off-chip pulsers. FIG. 5 shows an example of this configuration. The resulting beam forming for therapy is fixed (e.g., focusing in the center of the imaging field of view). In other cases, each pixel switch is configured to connect or disconnect its corresponding transducer element to a selectable one of the off-chip pulsers. FIG. 7 shows an example of this configuration, where line switch 702 selects the line of bus 110 that is connected to block 504. The resulting beam forming for therapy is adjustable. For example, the therapy beam can be brought to a focus at any selected location within the imaging field of view. As another example, the therapy beam could be configured to scan within the imaging field of view along any desired path.

Practice of the invention does not depend critically on details of how integration is performed, provided that the pulsers for the therapy mode are not integrated with the transducer chip. FIG. 1 shows a two-chip hybrid bonded configuration. In the specific example given above, both the first electronic circuitry (for imaging) and the mode control circuitry (for switching) were included in chip 104. Other two-chip configurations can be obtained by moving the imaging or switching circuitry to be monolithically integrated with transducer chip 102. In these cases, chip 104 will have only the switching circuitry or only the imaging circuitry, respectively.

Three-chip configurations are also possible. FIG. 8 shows an example, where a switch chip 802 and an imaging chip 804 are integrated with transducer array 102. Here it is assumed that mode switching circuitry 808 is on the top side of switch chip 802, and that through-chip vias 810 are used to connect mode switching circuitry 808 to imaging chip 804. Imaging chip 804 is flip chip bonded (806) to switch chip 802.

A final possibility is full monolithic integration of everything except the off-chip pulsers. FIG. 9 shows a example of this approach. Here the first electronic circuitry (for imaging), the second electronic circuitry (except for pulsers 108) and the mode switching circuitry are all monolithically integrated on transducer chip 902.

The invention claimed is:

1. An apparatus for ultrasonic imaging and therapy, the apparatus comprising:
   an array of transducer elements;
   imaging circuitry configured to perform ultrasound imaging with the array of transducer elements in an ultrasonic imaging mode;
   a pulser configured to provide a voltage to a transducer element of the array of transducer elements in an ultrasound therapy mode; and
   mode switching circuitry connected between the pulser and the transducer element, the mode switching circuitry configured to switch operation of the transducer element between the ultrasonic therapy mode and the ultrasonic imaging mode, the mode switching circuitry comprising transistors arranged to pass a voltage that is greater than a gate-to-source voltage of any one of the transistors.

2. The apparatus of claim 1, further comprising:
   one or more additional pulsers, wherein the pulser and the one or more additional pulsers are included in a plurality of pulsers; and
   a line switch configured to connect the mode switching circuitry to a selected one of the pulsers.

3. The apparatus of claim 1, wherein the transistors comprise a first transistor and a second transistor connected in series with each other, and wherein the switch comprises a diode connected between a source and a gate of the first transistor, the diode also being connected between a source and a gate of the second transistor.

4. The apparatus of claim 1, wherein the imaging circuitry and the mode switching circuitry are integrated on a chip, and wherein the pulser is external to the chip.

5. The apparatus of claim 1, wherein the transducer elements are capacitive micromachined ultrasonic transducers.

6. An apparatus for ultrasonic imaging and therapy, the apparatus comprising:
   an array of transducer elements;
   imaging circuitry on a chip, the imaging circuitry configured to perform ultrasound imaging with the array of transducer elements in an ultrasonic imaging mode;
   a pulser located external to the chip such that heat dissipation associated with the pulser occurs external to the chip;
   a switch configured to connect the pulser to a transducer element of the array of transducer elements for an ultrasonic therapy mode and to disconnect the pulser from the transducer of the array of transducers for an ultrasonic imaging mode; and
   a line switch configured to connect the switch to a selected one of a plurality of pulsers, wherein the pulsers comprise the pulser.

7. The apparatus of claim 6, further comprising an inductor in series between the switch and the transducer element, wherein a combination of the inductor and the transducer element is electrically resonant at an ultrasound therapy frequency of the ultrasonic therapy mode.

8. The apparatus of claim 6, wherein the array of transducer elements is arranged on a transducer chip, and wherein the transducer chip is integrated with the chip.

9. The apparatus of claim 8, wherein the switch is arranged on a switch chip that is integrated with the chip.

10. The apparatus of claim 6, wherein the switch is integrated on the chip.

11. The apparatus of claim 6, wherein the array of transducer elements is configured to transmit a therapy beam in the therapy mode, and wherein the apparatus is configured such that the therapy beam is adjustable.

12. The apparatus of claim 6, wherein the array of transducer elements comprises at least 32 transducer elements in a first dimension by 32 transducer elements in a second dimension.

13. The apparatus of claim 6, wherein the transducer elements are capacitive micromachined ultrasonic transducers.

14. An apparatus for ultrasonic imaging and therapy, the apparatus comprising:
   an array of transducer elements;
   imaging circuitry on a chip, the imaging circuitry configured to perform ultrasound imaging with the array of transducer elements in an ultrasonic imaging mode;
   a pulser located external to the chip such that heat dissipation associated with the pulser occurs external to the chip; and
   a switch configured to connect the pulser to a transducer element of the array of transducer elements for an ultrasonic therapy mode and to disconnect the pulser from the transducer of the array of transducers for an ultrasonic imaging mode, wherein the switch comprises transistors arranged to pass a voltage from the pulser that is greater than a gate-to-source voltage of any one of the transistors.

15. An apparatus for ultrasonic imaging and therapy, the apparatus comprising:
   an array of transducer elements;
   imaging circuitry on a chip, the imaging circuitry configured to perform ultrasound imaging with the array of transducer elements in an ultrasonic imaging mode;
   a pulser located external to the chip such that heat dissipation associated with the pulser occurs external to the chip; and
   a switch configured to connect the pulser to a transducer element of the array of transducer elements for an ultrasonic therapy mode and to disconnect the pulser from the transducer of the array of transducers for an ultrasonic imaging mode, wherein the transistors comprise a first transistor and a second transistor connected in series with each other, and wherein the switch comprises a diode connected between a source and a gate of the first transistor, the diode also being connected between a source and a gate of the second transistor.

16. The apparatus of claim 15, further comprising a line switch configured to connect the switch to a selected one of a plurality of pulsers, wherein the pulsers comprise the pulser.

17. The apparatus of claim 15, wherein the array of transducer elements is configured to transmit a therapy beam in the therapy mode, and wherein the apparatus is configured such that the therapy beam is adjustable.

18. The apparatus of claim 15, further comprising additional switches, wherein the switch and the additional switches are included in a plurality of switches, and wherein each of the transducer elements is connected to one switch of the plurality of switches.

19. A method of performing ultrasonic imaging and therapy with an array of ultrasonic transducers, the method comprising:

connecting a pulser to a selected ultrasonic transducer of the array of ultrasonic transducers for performing ultrasonic therapy;

while the pulser is connected to the selected ultrasonic transducer of the array of ultrasonic transducers, applying a voltage from the pulser to the selected ultrasonic transducer of the array of ultrasonic transducers using a switch, wherein the switch comprises transistors, and wherein the voltage is greater than a gate-to-source voltage of any one of the transistors;

disconnecting the selected ultrasonic transducer of the array of ultrasonic transducers from the pulser; and while the selected ultrasonic transducer of the array of ultrasonic transducers is disconnected from the pulser, performing ultrasonic imaging with an imaging circuit and the array of ultrasonic transducers.

20. The method of claim 19, further comprising adjusting a therapy beam transmitted from the array of ultrasonic transducers for performing ultrasonic therapy.

21. The method of claim 20, wherein the therapy beam is focused at a selected location.

22. The method of claim 19, further comprising connecting the selected ultrasonic transducer of the array of ultrasonic transducers to another pulser using the switch and a line switch, wherein the line switch is configured to connect the switch to a selected one of a plurality of pulsers, and wherein the plurality of pulsers comprises the pulser and the other pulser.

* * * * *